United States Patent [19]

Pollard et al.

[11] Patent Number: 4,670,394

[45] Date of Patent: Jun. 2, 1987

[54] ISOLATION AND CULTURE OF ADRENAL MEDULLARY ENDOTHELIAL CELLS PRODUCING BLOOD CLOTTING FACTOR VIII:C

[75] Inventors: Harvey B. Pollard, Potomac; Richard Ornberg, Bethesda; Dipak Banerjee, Rockville; Moussa Youdim, Rockville; Peter Lelkes, Rockville; Eli Heldman, Rockville, all of Md.

[73] Assignee: The United States of America as represented by the Secretary of the Department of Health and Human Services, Washington, D.C.

[21] Appl. No.: 672,451

[22] Filed: Nov. 16, 1984

[51] Int. Cl.[4] .................. C12N 5/00; C12P 21/00; C12R 1/91; A61K 35/14

[52] U.S. Cl. ........................ 435/240; 435/68; 435/948; 530/383

[58] Field of Search .............. 435/240, 68, 948; 424/101, 85; 260/112 R, 112 B; 530/383

[56] References Cited

U.S. PATENT DOCUMENTS

| | | | |
|---|---|---|---|
| 4,348,315 | 9/1982 | Blömbäck | 260/112 B |
| 4,370,264 | 1/1983 | Kotitschke et al. | 530/383 |
| 4,440,679 | 4/1984 | Fernandes et al. | 530/383 |
| 4,446,134 | 5/1984 | Naito et al. | 530/383 |
| 4,534,972 | 8/1985 | Lembach | 530/383 |
| 4,540,573 | 9/1985 | Neurath et al. | 530/383 |

OTHER PUBLICATIONS

Differential Monoamine Metabolism in Isolated Bovine Adrenal Medullary Endothelial Cells, Dipak K. Banerjee, Moussa B. H. Youdim and Harvey B. Pollard, J. Pharm. Pharmacol 36 (Suppl) 1984, 15 W Meeting Date, Aug. 4-6, 1984.

Synthesis of Factor VIII Antigen by Cultured Human Endothelial Cells, Eric A. Jaffe, Annals New York Academy of Sciences, 240:62-69, 1975.

An Osmotic Mechanism for Exocytosis from Dissociated Chromaffin Cells, Harvey B. Pollard, Christopher J. Pazoles, Carl E. Creutz, Janet H. Scott, Oren Zinder and Adair Hotchkiss, Journal of Biological Chemistry, vol. 259, No. 2, Jan. 25/84, pp. 1114-1121.

Hoyer, L. W. et al, "Localization in Endothelial Cells by Immunofluorescent Microscopy", 1973, *J. of Clin. Invest.*, vol. 52, 2737-2744.

Jaffe, E. A. et al., "Synthesis of Antihemophilic Factor Antigen by Cultured Human Endothelial Cells", *J. Clin. Invest.*, vol. 52, pp. 2757-2764, 1973.

Crickard, K., "Isolation and Identification of Human Fetal Adrenal Medullary Cells in Vitro", 1982, *J. Clin. Endocrin. Metab.*, vol. 55, pp. 1143-1148.

Eiden, L., "Synthesis and Release of Vasoactive Polypeptide", 1982, 66th Annual Mtg. of FASEB, Apr. 15-23, 1982, Fed. Proc. 41(4), 1982.

Banerjee, D. et al, "Cultured Endothelial Cells from Bovine Adrenal Medulla", *J. Cell Biology*, 1984, 99(4 Part 2), Mtg. Date, Nov. 12-16, 1984.

Warhol, M., "The Ultrastructural Localization of von Willebrand Factor", 1984, *American J. Pathology*, vol. 117, pp. 310-315.

Jaffe, E. A., R. L. Nachman, C. G. Becker and C. R. Minick, J. Clin. Invest. 52: 2745-2756.

Jaffe, E. A., *Ann. New York Acad. Sci.*, 401 (Endothelium): 163-170, 1982.

Jaffe, E. A., *Biology of Endothelial Cells*, Boston: Martinus Nijhoff Publishers, 1984, pp. 1-13, 59-65, 86-96, 108-117.

*Primary Examiner*—Thomas G. Wiseman
*Assistant Examiner*—Karen Maurey
*Attorney, Agent, or Firm*—Holman & Stern

[57] ABSTRACT

The present invention discloses a new line of endothelial cell of adrenal medullary origin capable of producing blood clotting Factor VIII:C. A method of isolating and culturing said cell line has also been disclosed. Factor VIII:C is useful in treating hemophilia.

10 Claims, 6 Drawing Figures

ISOLATION AND CULTURE OF ADRENAL MEDULLARY ENDOTHELIAL CELLS PRODUCING BLOOD CLOTTING FACTOR VIII:C

BACKGROUND OF THE INVENTION

1. Technical Field

The present invention is directed to isolation and culture of adrenal medullary endothelial cells. More particularly, the present invention is related to a method of isolating and culturing endothelial cells of adrenal medullary origin which produce blood clotting Factor VIII:C.

2. Prior Art

Factor VIII is a blood protein and a component of the normal human blood. It is generally recognized that Factor VIII has at least three different functional sub units: (a) Factor VIII antigen (VIII AGN); (b) Blood clotting factor (VIII:C) that corrects the blood coagulation abnormality in classic hemophilia (hemophilia A) sometimes also designated as (VIII:AHF); and (c) von Willebrand Factor (VIII: vWF or VIII:R). As used herein the term Factor VIII is defined as and specifically refers to only VIII:C, the anti-haemophilic blood clotting factor and none other, except when otherwise noted. The significance of this blood clotting Factor VIII, of course, can be easily understood from the fact that its deficiency results in a bleeding disease commonly known as hemophilia. Blood clotting Factor VIII is, therefore, required for the treatment of hemophilia.

Factor VIII: C is quite distinct from other blood protein components. As mentioned supra, Factor VIII deficiency is associated with classic hemophilia A and von Willebrand's disease. Without being bound to any theory, it is hypothesized that two separate proteins may be involved. One is FVIII/vWF protein which is a glycoprotein that is multimeric, with molecular weights ranging from 850,000 to 30 million. The second protein is a 200,000 MW glycoprotein noncovalently complexed to the FVIII/vWF protein. It has procoagulant activity, termed VIII:C. The function of FVIII/vWF is to promote adhesion of platelets with the collagen coat associated with endothelial cells. It is controlled by a gene on the X-chromosome. The drug ristocetin causes platelets to aggregate by interacting with FVIII/vWF protein attached to platelets. In this guise it is also called FVIII:R or FVIII:RCoF. "RCoF" stands for ristocetin cofactor. An additional function of FVIII:R (or FVIII/vWF) may be to stabilize circulating FVIII:C for elaboration of its activity. The antibody usually raised against crude Factor VIII preparations is against FVIII:R, also termed Factor VIII-related antigen in the immunologically oriented literature. The site of synthesis of these factors is still not precisely known. The protein that resembles FVIII:R (factor VIII-related antigen, FVIII/vWF) has been shown to be synthesized by endothelial cells. The procoagulant component of factor VIII comes from an yet unidentified source (*Fundamentals of Clinical Hematology*, ed. by J. L. Spivak, Harper and Row Publ., Philadelphia, 1984, pages 367–372).

Heretofore, Factor VIII has been conventionally obtained from blood concentrates that may contain the pooled plasma of up to 20,000 blood donors. In accordance with the presently known process of obtaining therapeutic amounts of Factor VIII, pooled human serum or plasma is first treated by freezing and a cryoprecipitate is prepared therefrom. After thawing, Factor VIII is then precipitated by centrifugation. The precipitate is then used as a therapeutic agent or drug.

In accordance with a recent report, it has been estimated that "Although annual production of Factor VIII concentrates is 900 million international units (IU), production of cryoprecipitate, a substance rich in Factor VIII, is less than 300 million IU. These current supplies are clearly insufficient for the world's needs". (American Red Cross, Blood Services Bulletin, Vol. 17, No. 9, page 1, Aug. 15, 1984.)

In addition, among the various disadvantages and limitations of the currently used plasma process for preparing Factor VIII, at least the following should be noted.

(1) Almost inevitable presence of hepatitis viruses in the pooled blood concentrate as a result of which many hemophiliacs suffer from liver dysfunction caused by non-A and non-B hepatitis when Factor VIII prepared from such blood concentrates is administered to hemophiliac patients.

(2) High risk of causing Acquired Immune Deficiency Syndrome (AIDS) in patients treated with Factor VIII obtained from plasma concentrate because of potentially certain contamination of such plasma with AIDS virus.

(3) Need for human donors of blood, therefore, limited availability of Factor VIII.

(4) Human Factor VIII is contraindicated for some hemophiliacs due to such persons' developing antibodies against Factor VIII; therefore, Factor VIII from non-human sources has been considered to be of particular value for treatment of such hemophiliacs.

Factor VIII:C of the present invention, described fully hereunder, is believed to be of great significance in treating blood clotting abnormality in humans without the fear or risks associated with the conventional plasma preparations.

It has been known that Factor VIII is localized in, hence a marker of, endothelial cells (Hoyer et al., 1973, J. Clin, Invest. 52:2737–2744). However, endothelial cells originating from different tissues have different, tissue-specific biochemical and endocrine functions. For instance, capillary endothelial cells in adipose tissue may be involved in specific lipolytic reactions (Scow et al, 1976, Circ. Res. 39:149–162), while those in the smooth muscle may synthesize and secrete potent smooth muscle relaxing factors affecting neurotransmitter receptors (Smith et al., 1972, Handbook of Exp. Pharmacol, 33:538–605). In the lung, on the other hand, the function of the endothelial cells may include lipid metabolism leading to prostaglandin and prostacyclin synthesis, selective metabolism of biogenic amines and other vasoactive substances such as angiotensin and the metabolism of platelet aggregating agent adenosine diphosphate.

Although endothelial cells from other tissues have been studied, endothelial cells from adrenal medulla have not heretofore been isolated and cultured. A problem encountered is that most endothelial cells grow so slowly in vitro that they are not of any significant value from a practical stand point. Furthermore, they usually are capable of only up to 30 cycles of division and then die.

The present invention for the first time provides a unique line of endothelial cells capable of continuous growth and a method of isolating and culturing in vitro said endothelial cells of adrenal medullary origin, which multiply profusely and produce blood clotting Factor VIII:C having none of the disadvantages or limitations of the conventionally used blood concentrate FVIII:C. The invention also provides for the first time the opportunity of studying various properties of endothelial cells including structural, physiological and biochemical attributes thereof.

SUMMARY

It is, therefore, an object of the present invention to provide a line of profusely growing endothelial cells from adrenal medulla capable of producing Factor VIII:C.

It is a further object of the present invention to provide a method of isolating and culturing endothelial cells of adrenal medullary origin which produce Factor VIII:C.

Other objects and advantages will become apparent as the description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein, FIG. 1 shows light microscopy of the endothelial cells in culture: Adrenal medullary endothelial cells were plated in two chamber glass slides at a cell density of $5 \times 10^3$ in 3 ml of medium. The cells were incubated at 37° C. in presence of 5% $CO_2$ and at desired time the slides were removed, cells were washed and mounted with a cover slip. The pictures were taken with Nomarski interference contrast on Zeiss Ultraphot II inverted microscope. Sequentially the pictures are (a) 1 day old culture, (b) 2 days old culture and (c) 8 days old culture taken at a magnification of $\times 80$.

(a) Low magnification view of putative precapillary lumens (*) formed by juxtaposed endothelial cells. The lumens are free of extracellular matrix ($\times 14,500$).

(b) Extracellular matrix being exocytotically released and presumably transforming from a nebulous web (lower arrow) into parallel filamentous strands (upper arrow). Magnification $\times 94,000$ (c) Cross section view of mitochondria typical of these endothelial cells. Such expansive views are common when cells are sectioned paralled to their long axis ($\times 17,000$).

(d) Vesicular shuttling or transcytosis (arrow) between putative precapillary lumen (*) and a thin intercellular space ($\times 71,000$).

(e) Gap junction typical of contacts between endothelial cells ($\times 169,000$).

(f) Intercellular filaments which predominate cell juxtapositions where precapillary lumens (*) form. These fine filaments are very similar to those seen between the endothelial pedicels in the renal corpuscle ($\times 34,500$);

FIG. 5 shows growth and proliferation of endothelial cells. The monolayer culture of endothelial cells was trypsinized for 5 min at 37° C. After removal of trypsin, the cells were suspended in complete medium (MEM) and then plated into 24-well culture plates (diameter 1.8 cm/well) at a concentration of $5 \times 10^4$ cells/well. At the indicated time, cells were trypsinized and counted using hemocytometer. Each point represents a mean from three wells. In parallel rows of well 0.01 $\mu$Ci of 2-($^{14}$C)-thymidine (50 mCi/mmol) and 1 $\mu$Ci of ($^{14}$C)-leucine (300 mCi/mmol) in 1 ml MEM were added at 24 hours interval. 24 hours later cells were harvested from each well following trypsinization and precipitated with 10% TCA. The precipitates were washed over 0.45$\mu$ millipore filters and counted in hydrofluor. Each point is the mean from three wells.

DETAILED DESCRIPTION OF THE INVENTION

These and other objects and advantages of the present invention are achieved by in vitro culturing of adrenal medullary endothelial cells, comprising the steps of dissociating adrenal medullary cells from an adrenal gland and allowing said cells to incubate and proliferate in a medium and environment suitable for the growth of said cells and then isolating therefrom endothelial cells producing blood clotting Factor VIII:C and a line of endothelial cells so produced. A deposit of a line of said endothelial cell has been made in the American Type Culture collection, Rockville, Md. and assigned an accession number CRL 8659.

Although adrenal medulla from any suitable source can be used for the practice of the present invention, a preferred source is a non-chromaffin cell line from bovine adrenal medulla as a source of endothelial cells. As will be evident from the detailed description presented herein infra, one of the distinctive features of the endothelial cell line of the present invention is that, unlike the requirements of endothelial cells from other tissues, the adrenal medullary endothelial culture of the present invention grows on plastic surfaces in the absence of special growth factors and eventually differentiates to form organized longitudinal bundles of cells, structurally reminiscent of true capillaries. These cells also exhibit a profound, positive reaction for Factor VIII antigen, the classical marker for endothelial cells and are capable of inactivating vasoactive substances by a process of uptake and enzymatic degradation quite distinct from similar processes in the endocrine chromaffin cells (Youdim et al., 1984, Fed. Proc. 43:1582).

Preferred methods and materials used in the practice of the present invention are now described. All publications mentioned hereunder are incorporated herein by reference.

MATERIALS AND METHODS

Isolation of Endothelial Cells

Dissociated adrenal medullary cells are prepared by collagenase digestion of bovine adrenal gland. Adrenal glands from steers of cows were obtained at a local slaughter house and transported to the laboratory on ice within 2 hours of slaughter. Chromaffin cells were prepared by a modification of previously described methods in Hochman, et al., 1976, Biochem. Biophys. Acta, 421, pages 168-0175; Schneider et al., 1977, Proc. Natl. Acad. Sci. USA 74, pages 5036-5040; Brooks, 1977, Endocrinology 101, pages 1369-1378; Fenwick, et al., 1978, J. Cell Biol. 76, pages 12-30; Greenberg et al. 1982, Cell Tissue Res. 226, page 655. Glands were perfused through the adrenal vein at room temperature with a standard medium consisting of 118 mM NaCl, 3.3 mM KCl, 1 mM $MgSO_4$, 2.2 mM $CaCl_2$, 10 mM glucose, and 25 mM Hepes —NaOH buffer, pH 7.3. This operation was performed 4 times at 15-minute intervals and resulted in the removal of most of the blood. The glands were then perfused through the adrenal vein with 0.1% collagenase dissolved in the same medium and allowed to incubate at 37° C. for 15 minutes. This second operation was also performed 3 more times at 15-minute intervals. At this point the gland had become physically soft and droopy. The glands were then sliced open around their periphery at room temperature and then softened chromaffin tissue removed and placed in a petri dish with a minimal volume of collagenase solution. The tissue was then minced into approximately 1-$mm^2$ pieces with scissors and the free cells and solution were then filtered away through a 200-mesh nylon screen. The pieces of tissue, in a packed volume of 5 ml, were subsequently mixed with 25 ml of collagenase solution and shaken at 1 excursion/second at 37° C. in a Dubnoff metabolic shaker.

After 30 minutes of this treatment, cells were separated from undigested tissue by filtration through a nylon mesh and were then sedimented at $50 \times g$ for 5 minutes at room temperature on a Sorvall GLC-3 benchtop centrifuge. Cells were then washed three times in 20-ml portions of standard medium supplemented with 1% bovine serum albumin. Each wash was terminated by centrifugation as described above and cells were subsequently resuspended in fresh albumin solution by gentle swirling. Cells were finally placed in albumin solution, sealed and allowed to shake at 37° C. until needed. This interval seldom exceeded 10-15 minutes. Just before the cells were used in an experiment they were filtered once again, sedimented, resuspended in albumin solution, and placed at room temperature. Cell viability was assessed by trypan blue exclusion or by capacity to be stained by the vital dye natural red. The latter dye was considered to be better for this purpose because as the number of neutral red stained cells increased so did the magnitude of the secretion response. The typical preparation from 7-9 glands contained $0.5-1.0 \times 10^9$ chromaffin cells and was essentially free ($<<1\%$) of red blood cells. An occasional ($<1\%$) large adrenal cortical cell was noted which had a foamy cytoplasm and was nonreactive to the Falck-Hillarp cytochemical test for catecholamines. The dissociated non-chromaffin cells are then obtained by culturing for 3 hours at 37° C. in a 35 mm petri dish in a total volume of 3 ml at a cell density of $3 \times 10^5$ cells/dish in a medium comprising minimal essential medium (MEM, Gibco, N.Y.) supplemented with about 10% fetal calf serum (heat inactivated), glutamine (2 mM), penicillin (50 units/ml) and streptomycin (50 $\mu$g/ml). After the three hour period, unattached chromaffin and other cells are removed by aspiration and the dish replenished with 3 ml of fresh medium. The plate is then placed in a $CO_2$ incubator and left undisturbed for 5 days. The medium is poured off. The cells are then washed quickly with about 5 ml of trypsin solution containing about 0.25% trypsin, 0.1% EDTA in Dulbecco's phosphate buffer saline, pH 7.4. 2 ml of fresh trypsin solution is added and the cells are left at room temperature for about 5 minutes. The action of trypsin is stopped by adding about 10 ml of incubation medium. Uniform cell suspension is prepared by gently pipetting the trypsinized cells up and down for three times just enough to break clumps. The cell numbers in each suspension is determined by counting the cells in a hemocytometer under ordinary light microscope. Required number of cells are plated in fresh medium and incubated at 37° C. in a $CO_2$-incubator. At confluency, the entire procedure is repeated. $10^4$ cells seeded in either 75 $Cm^2$ flasks (falcon) or 60 mm plastic petri dishes are satisfactory for culture purposes.

Electron and Light Microscopy

Cultured cells are prepared for conventional thin section electron microscopy by fixation according to the method of Karnovsky, 1965, J. Cell Biol. 27:137A, followed by post-fixation in 4% osmium tetroxide in 0.1M cacodylate buffer, pH 7.4 at 0° C. for one hour. The cultures are subsequently stained enbloc in 1% uranyl acetate in acetate buffer, pH 5.0 at 8° C. for 12 hours followed by dehydration in graded ethanols and embedded in Araldite CY212 resin. Thin sections, 50-60 nm thick, are stained with uranyl acetate and lead citrate in a LKB Ultrostainer and examined at 80 KV in a Phillips electron microscope, model EM 400.

Staining for Factor VIII Components

Cells are dissociated in trypsin, plated on chamber slides and allowed to grow for various times. Subsequently, the cells are fixed in 100% methanol for 6 minutes at $-20°$ C., washed in standard phosphate-buffer-saline (PBS), pH 7.4, at room temperature and then incubated for 60 minutes at 37° C. with rabbit antiserum to human Factor VIII antigen (Calbiochem-Behring), diluted 1:80 in Dulbecco's Modified Eagle Medium (Gibco, N.Y.). Following the incubation, cells are washed 3 times at 5 minute intervals in PBS and then incubated with fluorescein-conjugated anti-rabbit IgG (Capell Laboratories), diluted 1:20 in PBS, for 60 minutes at room temperature. After washing twice in PBS (pH 7.4), the slides are examined for fluorescence according to the method of Hoyer et al, supra, which is incorporated herein by reference.

Figure 6A:
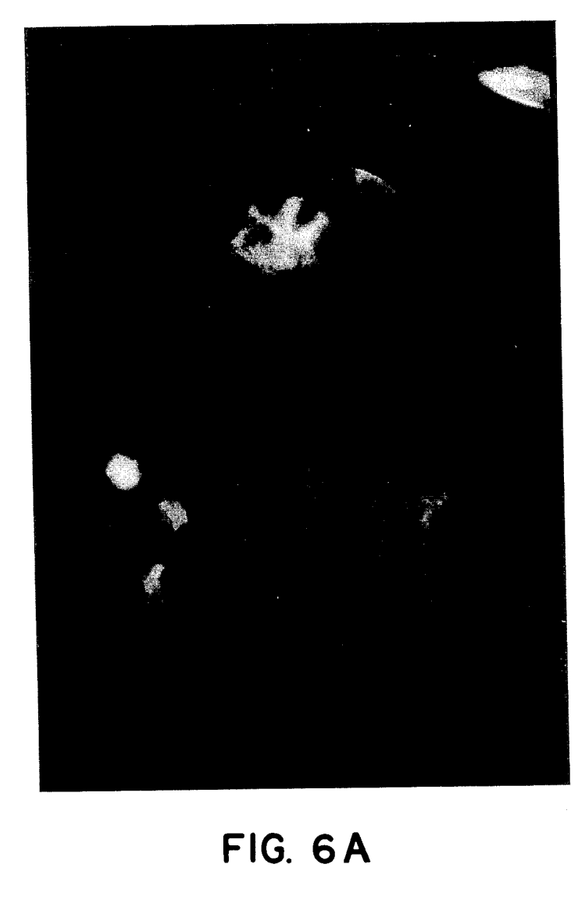
FIG. 6 shows the reactivity of anti-Factor VIII:C with cultured endothelial cells of the present invention.
Figure 6B:
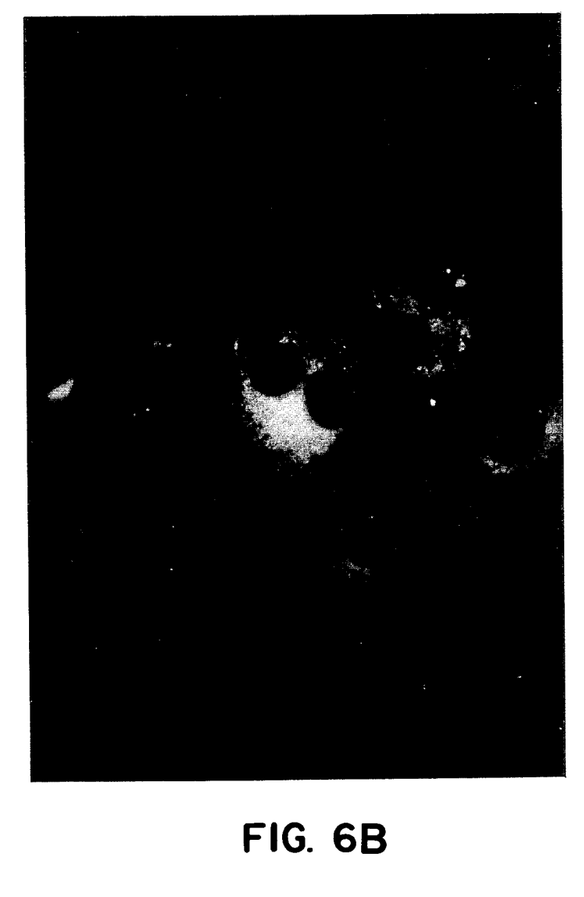

The cells were also found to be positive for Factor VIII:C, using a monoclonal antibody specific to Factor VIII:C, obtained from the Hybritech, Inc., Palo Alto, Calif. FIG. 6 shows the reaction of the anti-Factor VIII:C with cultured endothelial cells of the present invention.

Preparation of Blood Clotting Factor VIII:C

Blood clotting Factor VIII:C is released by the endothelial cells of the present invention in the growth medium. Hence, in order to obtain said factor VIII:C, the medium is separated from the endothelial cells by any standard means, such as pouring off, centrifugation, filtration and the like and the medium is then treated similar to the plasma process for obtaining Factor VIII:C which is a well established technique described in Technical Manual of the American Association of Blood Banks, Washington, D.C., 8th Edition, 1981 pages 44-47, and incorporated herein by reference.

Growth Curve for Endothelial Cells

For analysis of the growth rate, cultured endothelial cells are trypsinized for 5 minutes at 37° C., suspended in MEM, (Gibco, N.Y.) and then plated into 24-well culture plates at a concentration of $5 \times 10^4$ cells/well. At different times, cells are trypsinized and counted with a hemocytometer. $^{14}C$ Thymidine and $^{14}C$ leucine incorporation studies are performed in 1 ml of MEM following standard procedures. At different times, the cells are trypsinized and the cell suspension adjusted to 10% trichloroacetic acid. The precipitate is then collected on 0.45 micron millipore filters and counted in hydrofluor in a Beckman LS 9000 Liquid Scintillation Spectrometer.

RESULTS

The Nature of Capillaries in Adrenal Medulla Tissue

Adrenal medullary tissues from cow and rat are cut free-hand, mounted on a planchet and rapidly frozen on a copper block cooled in liquid helium. The tissue is found to contain abundant fenestrated capillaries bounded by nucleated endothelial cells and contained erythrocytes. This is similar to the data reported in a modern histology textbook where the tissues were fixed by conventional aldehyde fixation technique ("Histology" eds. Weiss and Greep, McGraw-Hill, N.Y. 1983, pages 373-420 and 842). Older histological texts have described adrenal medullary tissue as being particularly enriched in capillaries composed of typical endothelial cells.

Figure 1A:
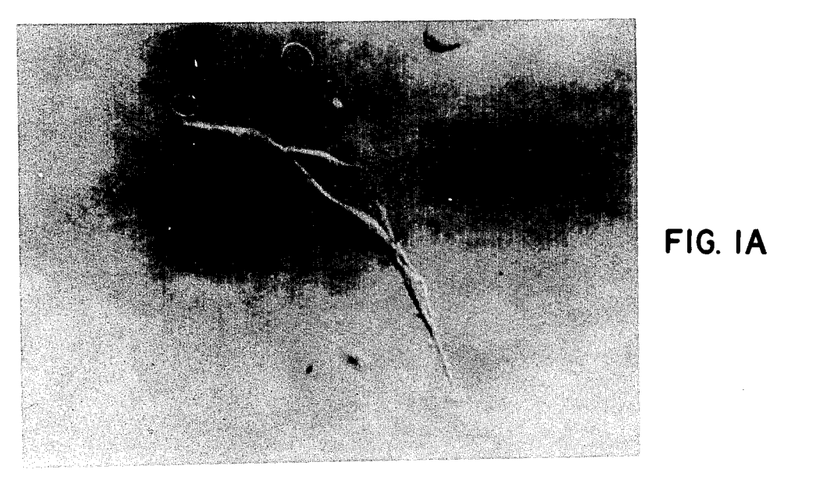
Figure 1B:
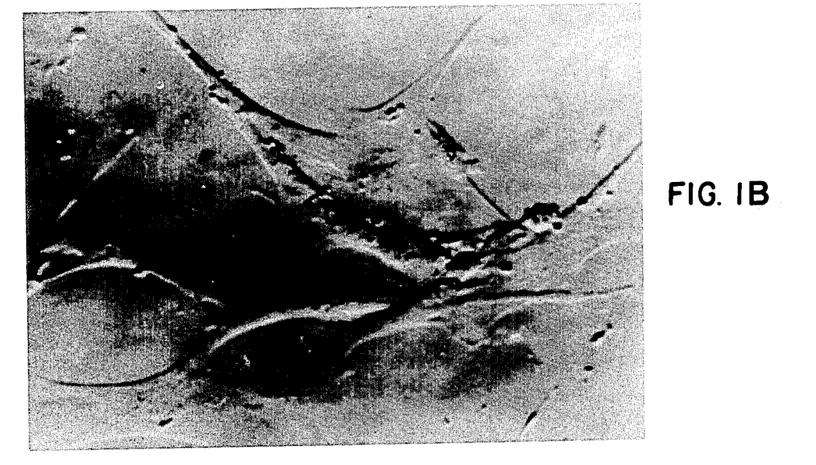
Figure 1C:
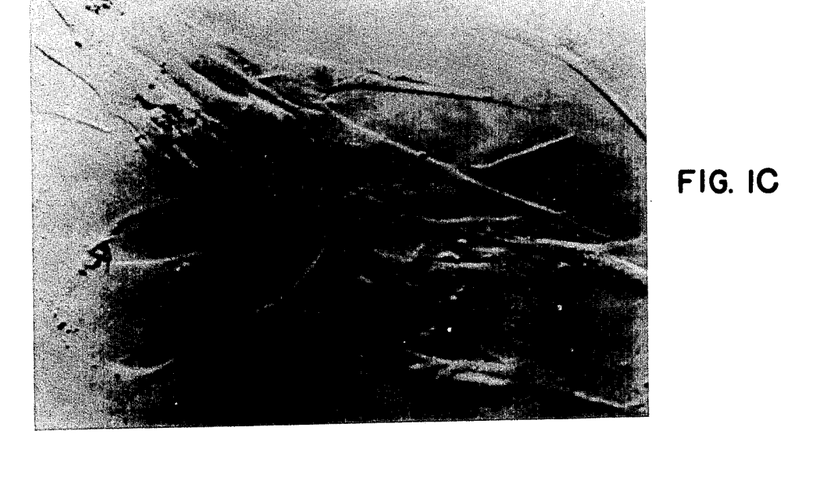

Observation of Capillary-Like Structures in Cells Cultured From Adrenal Medulla Dissociated cells from adrenal medulla are differently plated as described herein supra and attached cells allowed to grow. These growing cells initially exhibit a fusiform appearance upon attachment, and are frequently seen to be attached to one another in an end-to-end and side-to-side fashion (FIG. 1a). In succeeding days they become more flattened and elongated and exhibit more contact (FIG. 1b). By the eighth day in culture, extensive and ordered networks of cells can be observed (FIG. 1c).

Figure 2:
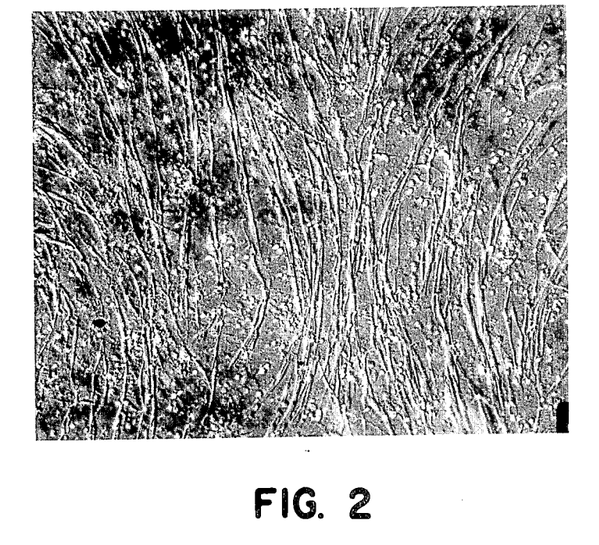
FIG. 2 shows cells grown in 75 $cm^2$ plastic flask for 3 weeks at 37° C. and in presence of 5% $CO_2$. At the end microscopic picture was taken on a Zeiss inverted microscope with Hoffman optics.

These cells are then allowed to remain in the incubator for up to three weeks without subculturing, but with changes of medium every 7 days. A rather spectacular change in the macroscopic structure of the cultures is then observed, in which numerous sets of parallel lines appear extending over a square centimeter in area. The nature of this organization is seen under low-power microscopy (FIG. 2) as numerous cords of cells lined up in parallel. These parallel cords of cells, which are interspersed in other groups of cords of cells, are organized into loops and whorls, and are embedded in a thin, elastic matrix which covers the entire surface of the flask. The individual cords of cells appear to have capillary-like character, and are therefore examined by chemical and electron microscopic criteria to determine if they are indeed capillaries.

Factor VIII:R and Factor VIII:C in Cultured Cells From Adrenal Medulla

Figure 3:
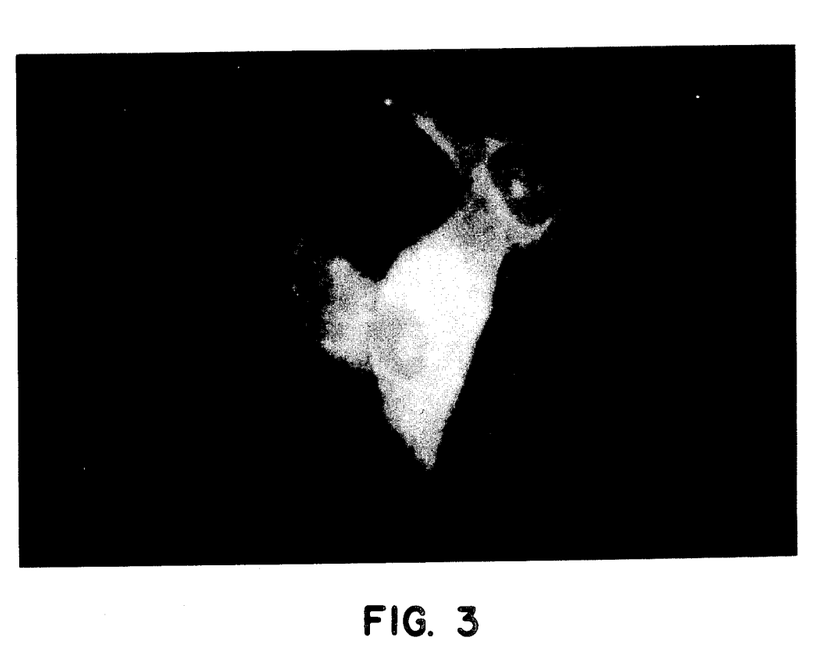
FIG. 3 shows immunofluorescence of Factor VIII in the endothelial cells: Adrenal medullary endothelial cells were grown in two-chamber glass slides. At the end of the incubation period the cells were washed and specific staining for Factor VIII antigen was performed as described in the text. The cells were three days old in culture. The photograph was taken at a magnification of $\times 250$.

Antigen associated with anti hemophilia factor, Factor VIII:R, which is present in endothelial cells, is known to be localized in capillaries, megakaryocytes and platelets (Hoyer et al, supra). Accordingly, the presence of Factor VIII:R was examined by immunocytochemistry and it was found as shown in FIG. 3, that these cells in culture of ages from day 1 to 3 weeks are heavily stained by anti-Factor VIII:R antibody. In parallel, conventional cultures of endothelial cells from bovine adrenal cortex were also stained, but it failed to show a positive reaction with fibroblast cell lines either from mouse (NIH 3T3) and human sources, or with cultured chromaffin cells from bovine adrenal medulla. Therefore, it was concluded that the cultured cells were indeed endothelial in nature, and that the organotypic structures they spontaneously generate in culture are apparently capillaries.

The endothelial cells of the present invention were also examined for Factor VIII:C, the blood clotting factor. Until now, the origin of this factor in the body was not known. However, using monoclonal antibodies to Factor VIII:C, obtained from both Hybritech (California) and Boehringer-Mannheim (California), Factor VIII:C, was found to be localized in subcellular organelles within the cells as shown in FIG. 6.

Electron Microscopic Structure of Cultured Cells

The observation that the cultured cells differentiated and formed capillaries could only be tested by electron microscopy. Indeed, electron microscopic examination confirmed that cells cultured over the entire 3 week period displayed cellular and organotypic morphologies characteristic of capillary endothelial cells. In cross-section, the cultured cells are flattened except at the nucleus, with thin processes extending for surprisingly long distances (FIG. 4A). The cytoplasm was filled with rough endoplasmic reticulum containing a dense matrix (FIG. 4B), and it became more specialized in the flattened processes where bundles of actin stress fibers and microtubules predominated. Dispersed mitochondria of the long tubular type (FIG. 4C) are frequently seen, whose elongated axes run parallel to the cellular axis defined by the flattened process.

Numerous surface cisterns of smooth, coated vesicles and small vesicles exhibiting exocytotic and endocytotic phenomena are also seen to underly and stud the plasmalemma (FIG. 4B and FIG. 4D). Images of vesicular shuttling ("transcytosis"), the sine qua non of capillary endothelia are often observed in 8 days and older cultures. Exocytosis of extracellular matrix is also observed (Arrow in FIG. 4B). This matrix material forms a nebulous web that rearrange into the more fibrillar backbone typical of capillary basal lamina adhering to the plasmalemma.

A number of specific intercellular structures characteristic of endothelial cells in capillaries are also present in 8 days and older cultures. These interactions include both tight and gap junctions (FIG. 4E), intercellular filaments (FIG. 4F) and intercellular spaces reminiscent of capillary lumens (FIG. 4A, 4F). Tight junctions and gap junctions are common in places where neighboring cells form boundaries of capillary lumens, and where neighboring fine strand processes attach the cells to one another FIG. 4B.

Fine stranded filaments (10 nm in diameter), quite distinct and physically separated from extracellular matrix and basal lamina, form a second kind of interaction between these cells (FIG. 4F). These fine filaments pass between juxtaposed plasma membranes over distances of tens of nanometers from separate membrane insertion points. Such intercellular filaments have not heretofore been known to have been described for other endothelial cells cultured in vitro. However, they are very similar to filaments which connect endothelial pedicels found between the basement membrane and Bowman's space in the renal corpuscle of the kidney ("Histology", supra, at p. 842).

Cytokinetics of Endothelial Cells

Figure 5:
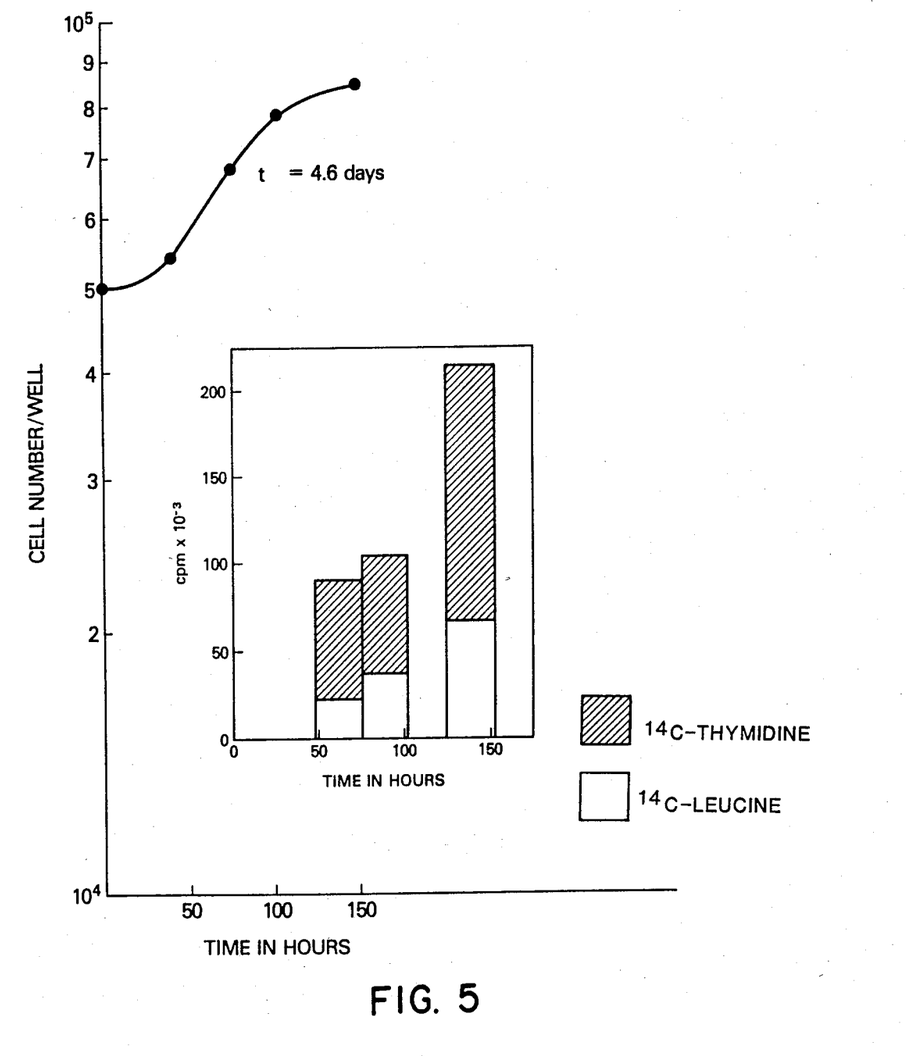

The endothelial cells of the present invention are readily subcultured by dissociation in trypsin and plating at low density in fresh media. As shown in FIG. 5, the doubling time for these cells was 4.6 days. Coincident with this doubling in cell number, we have also observed increase in ($^{14}$C)-thymidine and ($^{14}$C)-leucine incorporation consistent with the cell division and protein synthesis needed for growth (FIG. 5). The presence of L-tyrosine, an essential amino acid, was necessary for the growth and could not be replaced by L-phenylalanine, indicating that the cells do not contain phenylalanine hydroxylase. Moreover, cytosine arabinoside (10 μM) completely inhibited the cell growth.

Figure 4:
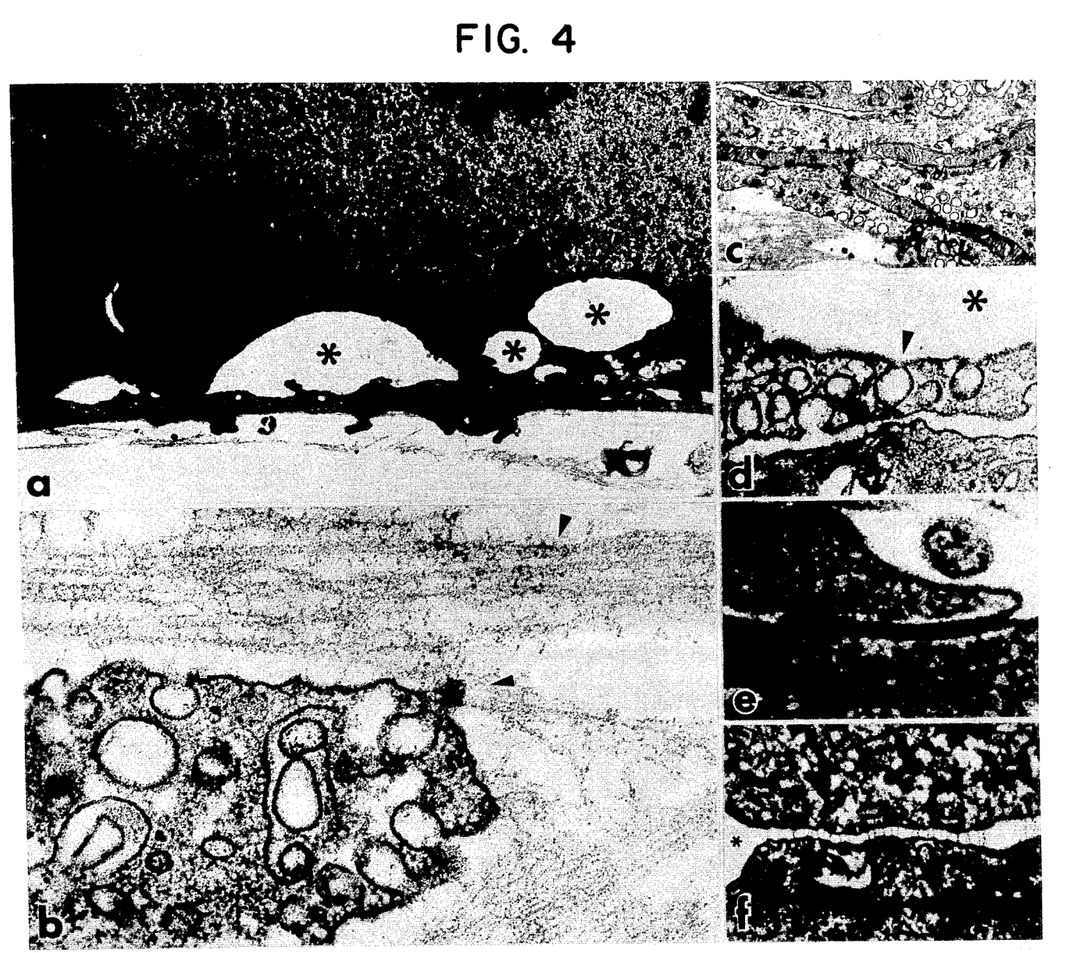
FIG. 4 shows capillary and endothelial types of ultra-structure from 8 days old endothelial cell cultures.

It is clear from the above description that endothelial cells from the bovine adrenal medulla grow in a relatively simple medium, form specialized intercellular connections and eventually generate macroscopic capillary-like structures. This is in marked contrast to other kinds of endothelial cells hitherto known, where a variety of growth promoting factors, special gelatin substrates and overlays are required, and where the structures generated by the cells are by comparison relatively primitive as described by Folkman et al, (1979) Proc. Natl. Acad. Sci. USA, 76: 5217–5221; Thornton et al, (1983) Science 222: 623–625; Montesano et al (1983) J. Cell Biol. 97: 1648–1652; and Franke et al (1979) J. Cell Biol. 81: 570–580. Probably, adrenal medullary endothelial cells synthesize their own essential components required for growth and differentiation. As seen in FIG. 4, they produce their own basal lamina substratum, evidence for which includes direct microscopic observation of secretion and assembly of the characteristic basal lamina filaments. The ready availability of such cells by in vitro culture and having the capability of capillary formation in the absence of added factors as disclosed herein, constitute a vast simplification for cell-biological studies of these processes in adrenal medulla and perhaps other tissues where capillary proliferation is likely to play a central role in pathophysiology.

Previous studies on endothelial cells from other sources have emphasized distinct culture requirements for growth, possibly related to the size and nature of the originating blood vessels. In the adrenal medulla the originating vessels may be the extensive and defined endocrine capillary barrier separating chromaffin cells from the blood stream. Various substances from chromaffin cells may be produced including specific proteins, catecholamines, nucleotides and other molecules by both exocytotic and non-exocytotic secretion. It is likely that the endothelial cells cultured from adrenal medulla in accordance with the present in vitro process are probably derived from cells making up the specific endocrine barrier, although the evidence for this hypothesis remains indirect. However, if this is the case, then the chemical, structural, and metabolic properties of these cells may prove to be quite important for understanding the function of the adrenal gland, per se, in addition to their usefulness for producing blood clotting Factor VIII:C for the treatment of hemophilia.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A biologically pure culture of a profusely and continuously growing endothelial cell line of adrenal medullary origin.

2. The cell line of claim 1 having the properties of American Type Culture Collection accession number CRL 8659.

3. The cell line of claim 1 being of bovine adrenal medullary origin.

4. The cell line of claim 1 which produces blood clotting Factor VIII:C in recoverable amounts.

5. The cell line of claim 1 profusely and continuously growing on plastic surface in a nutrient culture medium unsupplemented with growth promoters.

6. A method of in vitro culturing of adrenal medullary endothelial cells comprising the steps of dissociating adrenal medullary cells from an adrenal gland, and allowing said cells to proliferate in a medium and environment suitable for the growth of said cells to form recoverable amounts of continuously growing adrenal medullary cells, and then isolating therefrom said endothelial cells.

7. The method of claim 6 wherein dissociating comprises treating said adrenal gland with collagenase.

8. The method of claim 6 wherein said medium comprises minimal essential medium supplemented with about 10% heat inactivated fetal calf serum, about 2mM glutamine and suitable amount of antibiotic to prevent growth of undesirable organisms.

9. The method of claim 8 wherein said cells are incubated at about 37° C. for about 3 hours in said medium.

10. The method of claim 6 wherein said endothelial cells produce blood-clotting Factor VIII:C in recoverable amounts.

* * * * *